(12) United States Patent
Ortiz et al.

(10) Patent No.: US 7,914,511 B2
(45) Date of Patent: Mar. 29, 2011

(54) USE OF BIOSURGICAL ADHESIVE AS BULKING AGENT

(75) Inventors: Mark S. Ortiz, Milford, OH (US);
Derek Rund, Centerville, OH (US);
Darrel M. Powell, Cincinnati, OH (US);
Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 802 days.

(21) Appl. No.: 11/550,628

(22) Filed: Oct. 18, 2006

(65) Prior Publication Data
US 2008/0154228 A1    Jun. 26, 2008

(51) Int. Cl.
*A61M 31/00* (2006.01)
(52) U.S. Cl. ............... 604/506; 604/502; 604/516
(58) Field of Classification Search ........ 604/502, 604/506, 513, 516; 606/213, 215, 216
See application file for complete search history.

(56) References Cited

U.S. PATENT DOCUMENTS

| | | | |
|---|---|---|---|
| 4,735,616 A | 4/1988 | Eibl et al. | |
| 4,766,898 A | 8/1988 | Hardy et al. | |
| 4,874,368 A | 10/1989 | Miller et al. | |
| 5,004,469 A | 4/1991 | Palmieri et al. | |
| 5,154,320 A | 10/1992 | Bolduc | |
| 5,254,113 A | 10/1993 | Wilk | |
| 5,312,333 A | 5/1994 | Churinetz et al. | |
| 5,324,305 A | 6/1994 | Kanner | |
| 5,372,585 A | 12/1994 | Tiefenbrun et al. | |
| 5,443,481 A | 8/1995 | Lee | |
| 5,474,540 A | 12/1995 | Miller et al. | |
| 5,529,577 A | 6/1996 | Hammerslag | |
| 5,582,596 A | 12/1996 | Fukunaga et al. | |
| 5,605,541 A | 2/1997 | Holm | |
| 5,718,711 A | 2/1998 | Berenstein et al. | |
| 5,752,965 A | 5/1998 | Francis et al. | |

(Continued)

FOREIGN PATENT DOCUMENTS

EP    0716833 A2    6/1996

(Continued)

OTHER PUBLICATIONS

Ikeda, et al.; "Auxiliary Tool for Device for Applying Adhesive on Living Tissue;" published in Japan [translated abstract for Patent Application No. JP2000286958]; Jun. 12, 2001, (1 page).

(Continued)

*Primary Examiner* — Kevin C Sirmons
*Assistant Examiner* — Bhisma Mehta
(74) *Attorney, Agent, or Firm* — Frost Brown Todd LLC

(57) ABSTRACT

An exemplary method of reducing the volume of a stomach comprises providing an adhesive applier and a biocompatible adhesive. The exemplary method further comprises introducing at least a portion of the adhesive applier into the stomach and dispensing the adhesive through the adhesive applier into the stomach. The adhesive may be applied between the submucosa and muscle layers of the stomach to reduce the volume of the stomach. The adhesive may alternatively be applied in layers onto the inner surface of the stomach. Alternatively, a non-expandable member may be introduced into the stomach, and an adhesive may be used to secure the non-expandable member to the stomach. Such uses may provide a treatment for morbid obesity. An adhesive may also be used to provide flow restriction, such as by injecting the adhesive between the submucosa and muscle layers of a cardia or rectum.

11 Claims, 10 Drawing Sheets

U.S. PATENT DOCUMENTS

| | | |
|---|---|---|
| 5,759,169 A | 6/1998 | Marx |
| 5,759,171 A | 6/1998 | Coelho et al. |
| 5,814,022 A | 9/1998 | Antanavich et al. |
| 5,844,087 A | 12/1998 | Zimmerman et al. |
| 5,895,412 A | 4/1999 | Tucker |
| 5,928,611 A | 7/1999 | Leung |
| 5,981,621 A | 11/1999 | Clark et al. |
| 6,007,515 A | 12/1999 | Epstein et al. |
| 6,010,714 A | 1/2000 | Leung et al. |
| 6,055,828 A | 5/2000 | Rivera et al. |
| 6,099,807 A | 8/2000 | Leung |
| 6,113,571 A | 9/2000 | Zinger et al. |
| 6,143,352 A | 11/2000 | Clark et al. |
| 6,143,805 A | 11/2000 | Hickey et al. |
| 6,162,239 A | 12/2000 | Manhes |
| 6,174,919 B1 | 1/2001 | Hickey |
| 6,183,593 B1 | 2/2001 | Narang et al. |
| 6,206,905 B1 | 3/2001 | Holm et al. |
| 6,217,603 B1 | 4/2001 | Clark et al. |
| 6,228,051 B1 | 5/2001 | Trumbull |
| 6,234,994 B1 | 5/2001 | Zinger |
| 6,245,933 B1 | 6/2001 | Malofsky et al. |
| 6,280,399 B1 | 8/2001 | Rossin et al. |
| 6,283,933 B1 | 9/2001 | D'Alessio et al. |
| 6,302,898 B1 | 10/2001 | Edwards et al. |
| 6,306,243 B1 | 10/2001 | Clark et al. |
| 6,310,166 B1 | 10/2001 | Hickey et al. |
| 6,322,852 B1 | 11/2001 | Leung |
| 6,325,810 B1 | 12/2001 | Hamilton et al. |
| 6,340,097 B1 | 1/2002 | D'Alessio et al. |
| 6,352,704 B1 | 3/2002 | Nicholson et al. |
| 6,372,313 B1 | 4/2002 | D'Alessio et al. |
| 6,376,019 B1 | 4/2002 | Leung |
| 6,394,975 B1 | 5/2002 | Epstein |
| 6,394,982 B1 | 5/2002 | Ehrenfels |
| 6,398,797 B2 | 6/2002 | Bombard et al. |
| 6,412,639 B1 | 7/2002 | Hickey |
| 6,420,590 B1 | 7/2002 | Badejo et al. |
| 6,425,704 B2 | 7/2002 | Voiers et al. |
| 6,428,233 B1 | 8/2002 | Clark et al. |
| 6,428,234 B1 | 8/2002 | Bobo et al. |
| 6,432,084 B1 | 8/2002 | Levinson et al. |
| 6,433,096 B1 | 8/2002 | Hickey et al. |
| 6,439,789 B1 | 8/2002 | Balance et al. |
| 6,454,739 B1 | 9/2002 | Chang |
| 6,455,064 B1 | 9/2002 | Narang et al. |
| 6,458,095 B1 | 10/2002 | Wirt et al. |
| 6,461,361 B1 | 10/2002 | Epstein |
| 6,461,367 B1 | 10/2002 | Kirsch et al. |
| 6,464,663 B1 | 10/2002 | Zinger |
| 6,468,520 B1 | 10/2002 | Rowe et al. |
| 6,471,670 B1 | 10/2002 | Enrenfels et al. |
| 6,478,191 B1 | 11/2002 | D'Alessio et al. |
| 6,488,197 B1 | 12/2002 | Whitman |
| 6,488,650 B1 | 12/2002 | Epstein et al. |
| 6,488,944 B2 | 12/2002 | Narang |
| 6,491,201 B1 | 12/2002 | Whitman |
| 6,494,896 B1 | 12/2002 | D'Alessio et al. |
| 6,512,023 B1 | 1/2003 | Malofsky et al. |
| 6,527,749 B1 | 3/2003 | Roby et al. |
| 6,540,716 B1 | 4/2003 | Holm |
| 6,540,789 B1 * | 4/2003 | Silverman et al. ......... 623/23.65 |
| 6,547,467 B2 | 4/2003 | Quintero |
| 6,565,840 B1 | 5/2003 | Clark et al. |
| 6,579,469 B1 | 6/2003 | Nicholson et al. |
| 6,585,967 B2 | 7/2003 | Narang et al. |
| 6,589,269 B2 | 7/2003 | Zhu et al. |
| 6,592,281 B2 | 7/2003 | Clark et al. |
| 6,595,940 B1 | 7/2003 | D'Alessio et al. |
| 6,602,496 B2 | 8/2003 | Hedgpeth et al. |
| 6,605,667 B1 | 8/2003 | Badejo et al. |
| 6,607,631 B1 | 8/2003 | Badejo et al. |
| 6,613,020 B1 | 9/2003 | Holm et al. |
| 6,616,019 B2 | 9/2003 | D'Alessio et al. |
| 6,620,846 B1 | 9/2003 | Jonn et al. |
| 6,637,967 B2 | 10/2003 | Bobo et al. |
| 6,666,873 B1 | 12/2003 | Cassell |
| 6,676,322 B1 | 1/2004 | Leung |
| 6,681,979 B2 | 1/2004 | Whitman |
| 6,695,199 B2 | 2/2004 | Whitman |
| 6,705,790 B2 | 3/2004 | Quintero et al. |
| 6,743,858 B2 | 6/2004 | Hickey et al. |
| 6,746,667 B2 | 6/2004 | Badejo et al. |
| 6,748,950 B2 | 6/2004 | Clark et al. |
| 6,764,467 B1 | 7/2004 | Roby et al. |
| 6,767,552 B2 | 7/2004 | Narang |
| 6,779,657 B2 | 8/2004 | Mainwaring et al. |
| 6,783,514 B2 | 8/2004 | Tovey et al. |
| 6,802,416 B1 | 10/2004 | D'Alessio et al. |
| 6,802,822 B1 | 10/2004 | Dodge |
| 6,811,341 B2 | 11/2004 | Crane |
| D500,085 S | 12/2004 | Cotter et al. |
| 6,837,027 B2 | 1/2005 | Hickey |
| 6,863,660 B2 | 3/2005 | Marx |
| 6,884,232 B1 | 4/2005 | Hagmann et al. |
| 6,896,684 B2 | 5/2005 | Monassevitch et al. |
| 6,896,838 B2 | 5/2005 | D'Alessio |
| 6,921,381 B2 | 7/2005 | Spero et al. |
| 6,942,875 B2 | 9/2005 | Hedgpeth |
| 6,960,040 B2 | 11/2005 | D'Alessio et al. |
| 7,037,344 B2 | 5/2006 | Kagan et al. |
| 2002/0012678 A1 | 1/2002 | Narang |
| 2002/0037310 A1 | 3/2002 | Jonn et al. |
| 2002/0048480 A1 | 4/2002 | D'Alessio et al. |
| 2002/0055573 A1 | 5/2002 | Malofsky et al. |
| 2002/0065336 A1 | 5/2002 | Hickey et al. |
| 2002/0119184 A1 | 8/2002 | Nicholson et al. |
| 2002/0147462 A1 | 10/2002 | Mair et al. |
| 2002/0156203 A1 | 10/2002 | Hickey et al. |
| 2002/0157675 A1 | 10/2002 | Clark et al. |
| 2002/0165483 A1 | 11/2002 | Miller et al. |
| 2002/0173770 A1 | 11/2002 | Flory et al. |
| 2002/0176732 A1 | 11/2002 | Quintero et al. |
| 2002/0176733 A1 | 11/2002 | Clark et al. |
| 2002/0185396 A1 | 12/2002 | Mainwaring et al. |
| 2002/0192011 A1 | 12/2002 | Bobo et al. |
| 2002/0192107 A1 | 12/2002 | Hickey |
| 2003/0007826 A1 | 1/2003 | Badejo et al. |
| 2003/0007946 A1 | 1/2003 | Narang et al. |
| 2003/0007947 A1 | 1/2003 | Narang |
| 2003/0007948 A1 | 1/2003 | Hedgpeth |
| 2003/0007949 A1 | 1/2003 | Hedgpeth et al. |
| 2003/0015557 A1 | 1/2003 | D'Alessio et al. |
| 2003/0031499 A1 | 2/2003 | Heard et al. |
| 2003/0032833 A1 | 2/2003 | Badejo et al. |
| 2003/0032967 A1 | 2/2003 | Park et al. |
| 2003/0039781 A1 | 2/2003 | D'Alessio et al. |
| 2003/0044219 A1 | 3/2003 | Quintero |
| 2003/0060380 A1 | 3/2003 | Ayarza et al. |
| 2003/0063944 A1 | 4/2003 | Leung |
| 2003/0080151 A1 | 5/2003 | D'Alessio et al. |
| 2003/0082116 A1 | 5/2003 | Badejo et al. |
| 2003/0096069 A1 | 5/2003 | D'Alessio |
| 2003/0149128 A1 | 8/2003 | Malofsky et al. |
| 2003/0181964 A1 | 9/2003 | Sharkey et al. |
| 2003/0202956 A1 | 10/2003 | Clark et al. |
| 2004/0026282 A1 | 2/2004 | D'Alessio et al. |
| 2004/0059283 A1 | 3/2004 | Kirwan et al. |
| 2004/0111115 A1 | 6/2004 | Maw |
| 2004/0120849 A1 | 6/2004 | Stewart et al. |
| 2004/0137067 A1 | 7/2004 | Narang et al. |
| 2004/0143290 A1 | 7/2004 | Brightbill |
| 2004/0151688 A1 | 8/2004 | Sherbondy et al. |
| 2004/0190975 A1 | 9/2004 | Goodman et al. |
| 2004/0223932 A1 | 11/2004 | Hedgpeth et al. |
| 2004/0223946 A1 | 11/2004 | Kidd et al. |
| 2004/0234578 A1 | 11/2004 | Chen et al. |
| 2004/0254561 A1 | 12/2004 | Stenton |
| 2005/0033328 A1 | 2/2005 | Laufer et al. |
| 2005/0042266 A1 | 2/2005 | Narang |
| 2005/0047846 A1 | 3/2005 | Narang et al. |
| 2005/0070934 A1 | 3/2005 | Tanaka et al. |
| 2005/0070935 A1 | 3/2005 | Ortiz |
| 2005/0070939 A1 | 3/2005 | Beaupre |
| 2005/0145671 A1 | 7/2005 | Viola |
| 2005/0147457 A1 | 7/2005 | Badejo et al. |
| 2005/0175395 A1 | 8/2005 | Quintero et al. |

| | | | |
|---|---|---|---|
| 2005/0182443 A1 | 8/2005 | Jonn et al. | |
| 2005/0184121 A1 | 8/2005 | Heinrich | |
| 2005/0192601 A1* | 9/2005 | Demarais | 606/151 |
| 2005/0220849 A1 | 10/2005 | Hickey | |
| 2005/0230453 A1 | 10/2005 | Viola | |
| 2005/0256446 A1 | 11/2005 | Criscuolo et al. | |
| 2006/0009099 A1 | 1/2006 | Jonn et al. | |

FOREIGN PATENT DOCUMENTS

| | | | |
|---|---|---|---|
| EP | 1078600 A2 | 2/2001 | |
| EP | 1159081 A1 | 12/2001 | |
| EP | 1381321 A2 | 1/2004 | |
| EP | 1113839 B1 | 11/2004 | |
| EP | 1073484 B1 | 8/2005 | |
| EP | 1411836 B1 | 10/2005 | |
| JP | 10262986 | 10/1998 | |
| JP | 2000217830 | 8/2000 | |
| JP | 2001157716 | 6/2001 | |
| JP | 2001190558 | 7/2001 | |
| JP | 2002233581 | 8/2002 | |
| JP | 2003126268 | 5/2003 | |
| JP | 2005028009 | 2/2005 | |
| JP | 2005169125 | 6/2005 | |
| WO | WO 92/09651 | 6/1992 | |
| WO | WO 95/31137 A1 | 11/1995 | |
| WO | WO 98/41154 A1 | 9/1998 | |
| WO | WO 99/17833 A1 | 4/1999 | |
| WO | WO 99/30629 A1 | 6/1999 | |
| WO | WO 01/12257 A1 | 2/2001 | |
| WO | WO 01/24869 A1 | 4/2001 | |
| WO | WO 01/62158 A2 | 8/2001 | |
| WO | WO 01/62162 A1 | 8/2001 | |
| WO | WO 01/62333 A1 | 8/2001 | |
| WO | WO 02/067785 A2 | 9/2002 | |
| WO | WO 03/088845 | 10/2003 | |

OTHER PUBLICATIONS

Ikeda, et al.; "Device for Applying Organism Tissue Adhesive;" published in Japan [translated abstract for Patent Application No. JP2000320375]; Jul. 17, 2001, (1 page).

Gomibuchi, Makoto; "Medical Adhesive Applicator;" published in Japan [translated abstract for Patent Application No. JP11023146]; Aug. 8, 2000 (1 page).

Ikeda, et al.; "Organism-Tissue Adhesive Applicator;" published in Japan [translated abstract for Patent Application No. JP2001033756]; Aug. 20, 2002, (1 page).

Ikeda, et al.; "Biological Tissue Adhesive Applicator;" published in Japan [translated abstract for Patent Application No. JP2001323890]; May 7, 2003, (1 page).

Arikawa, Seiki; "Biological Tissue Adhesive Applicator;" published in Japan [translated abstract for Patent Application No. JP2003273091]; Feb. 3, 2005, (1 page).

Keller, Wilhelm A.; "Applicator for Dispensing Appliance;" published in Japan [translated abstract for Patent Application No. JP2004358509]; Jun. 30, 2005, (1 page).

Sasaki, Hiroshi; "Adhesive Agent Applicator for Surigcal Operation;" published in Japan [translated abstract for Patent Application No. JP09076817]; Oct. 6, 1998, (1 page).

* cited by examiner

USE OF BIOSURGICAL ADHESIVE AS BULKING AGENT

BACKGROUND

Biosurgical adhesives have been used in a variety of ways in various medical procedures. An exemplary adhesive is disclosed in U.S. Pub. No. 2004/0190975, the disclosure of which is incorporated by reference herein. Similarly, a variety of devices and techniques have been used to deliver adhesives at various sites. While several systems and methods have been made and used for delivering adhesives, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
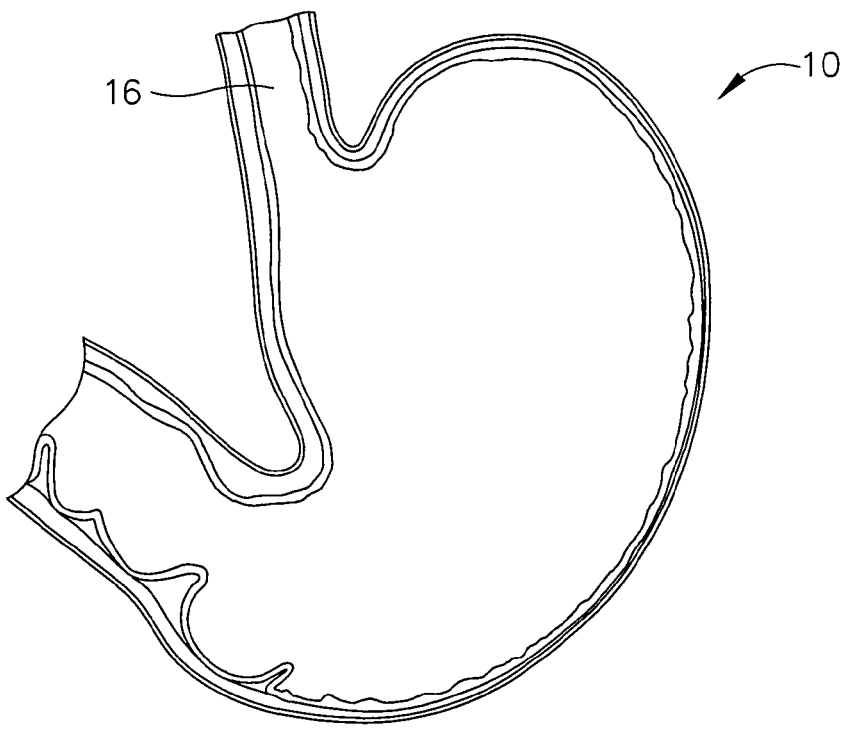
FIG. 1 depicts a plan view of a patient's stomach.
Figure 2:
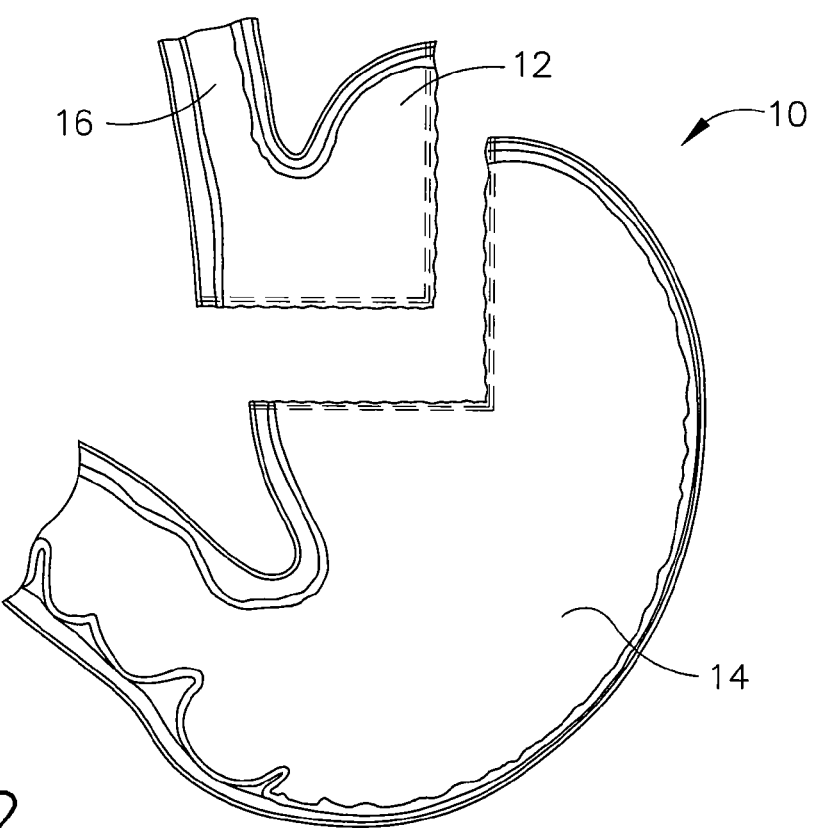
FIG. 2 depicts a plan view of the esophagus and a portion of the stomach of FIG. 1 separated from the remainder of the stomach in an exemplary fashion.
Figure 3:
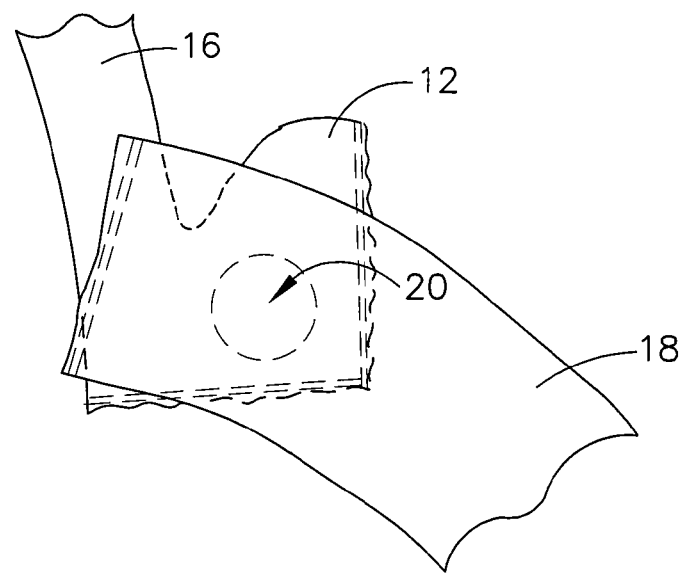
FIG. 3 depicts a plan view of a patient's intestine coupled with the stomach portion of FIG. 2 in an exemplary fashion.

FIGS. 1-3 show results of steps that may be performed during a conventional gastric bypass procedure, also known as a Roux-en-Y procedure. As shown, a patient's stomach (10) is separated into a first portion (12) and a second portion (14). The first portion (12) is adjacent to the esophagus (16), while the second portion (14) is adjacent to the small intestine (18). Along the line of separation, a series of staples are inserted to close off the separated ends of the first and second portions (12, 14), such that the first portion (12) forms a pouch. Next, a severed portion of the small intestine (18) (e.g., the jejunum) is joined to the first portion (12) of the stomach (10) via an anastomosis (20). By way of example only, the anastomosis (20) between the small intestine (18) and the first portion (12) of the stomach (10) may be provided by an anastomotic device, such as one disclosed in U.S. Pub. No. 2003/0032967 to Park et al., or one disclosed in U.S. Pub. No. 2005/0070934 to Tanaka et al., or one disclosed in U.S. Pub. No. 2005/0070935 to Ortiz, or one disclosed in U.S. Pub. No. 2005/0070939 to Beaupre, or using any other suitable device or technique. The disclosure of each of U.S. Pub. No. 2003/0032967 to Park et al., U.S. Pub. No. 2005/0070934 to Tanaka et al., U.S. Pub. No. 2005/0070935 to Ortiz, and U.S. Pub. No. 2005/0070939 to Beaupre is incorporated by reference herein. It will be appreciated that the foregoing description of a gastric bypass procedure is merely exemplary, and that a gastric bypass may be performed using a variety of alternative techniques. Furthermore, it will be appreciated that embodiments described herein may be used without any gastric bypass having been performed.

Figure 4:
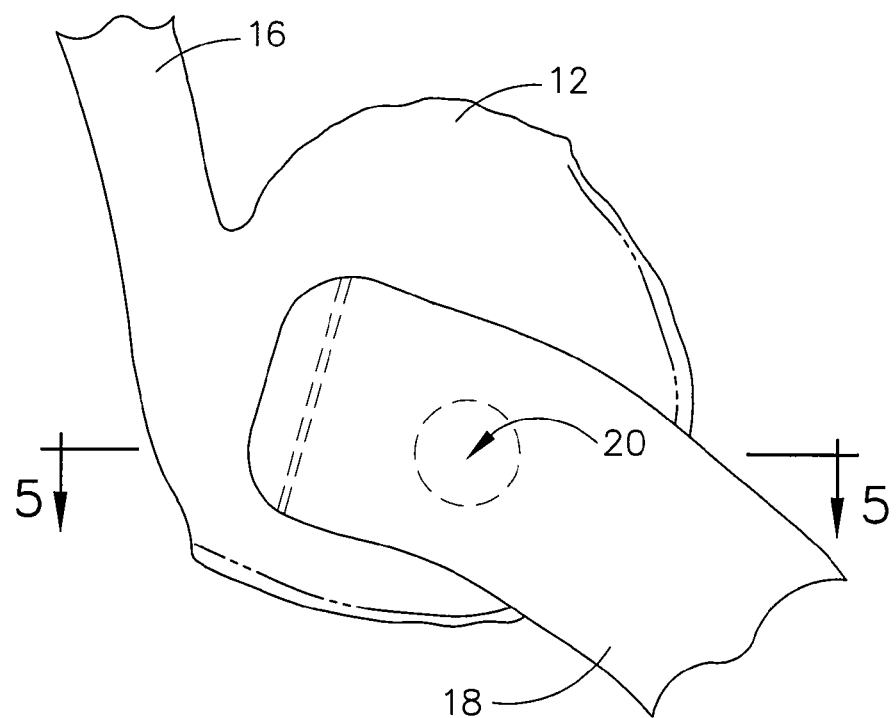
FIG. 4 depicts a plan view of the intestine and stomach portion combination of FIG. 3, with the stomach portion distended in an exemplary fashion.
Figure 5:
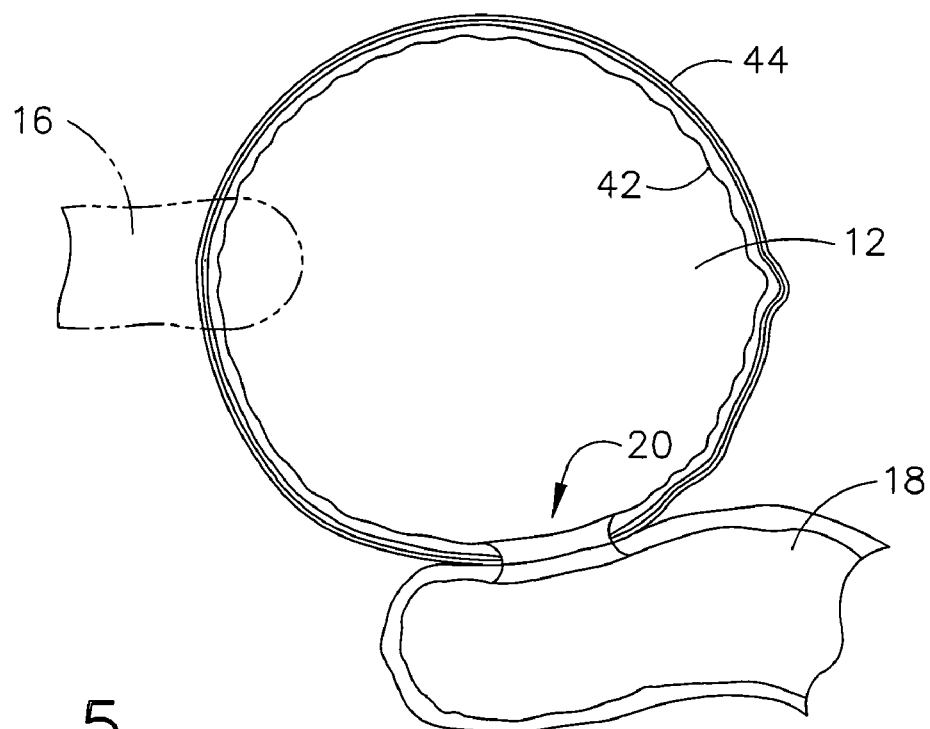
FIG. 5 depicts a cross-sectional view of the intestine and stomach portion combination of FIG. 4, taken along line 5-5 of FIG. 4.

In certain instances, the first portion (12) may undergo distention after a gastric bypass procedure has been completed. An example of such distention is illustrated in FIGS. 4-5. This distention may occur as a result of the patient overeating, or under other circumstances. It may be possible for such distention to essentially defeat the purpose of a gastric bypass procedure. There are a variety of ways in which such distention may be prevented or otherwise addressed.

Figure 6:
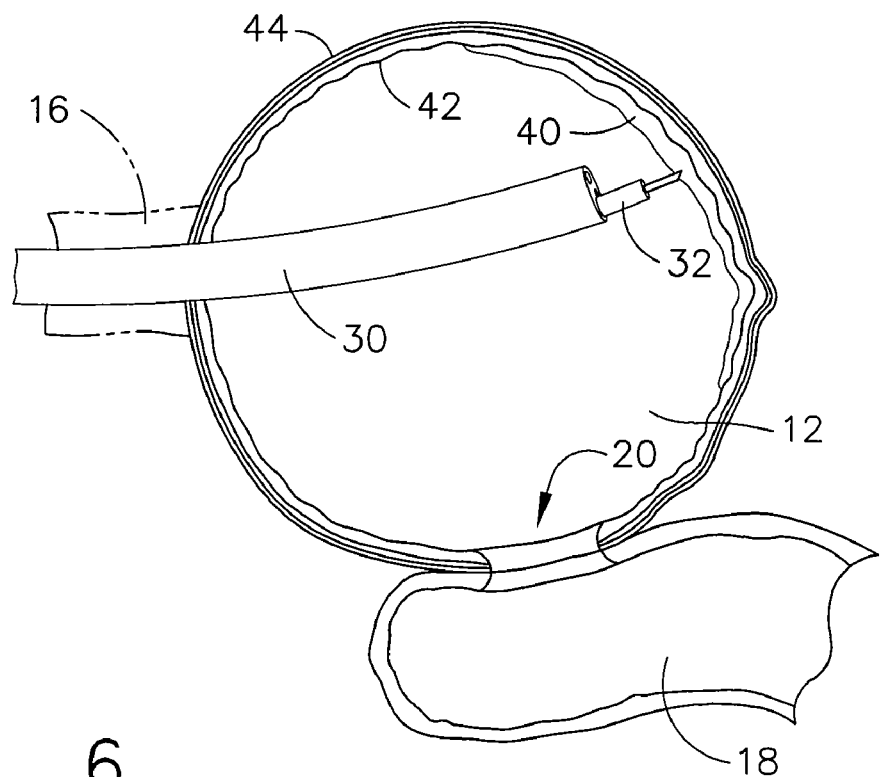
FIG. 6 depicts a cross-sectional view of an adhesive being applied to the stomach of FIG. 4 using an endoscope in an exemplary fashion.
Figure 7:
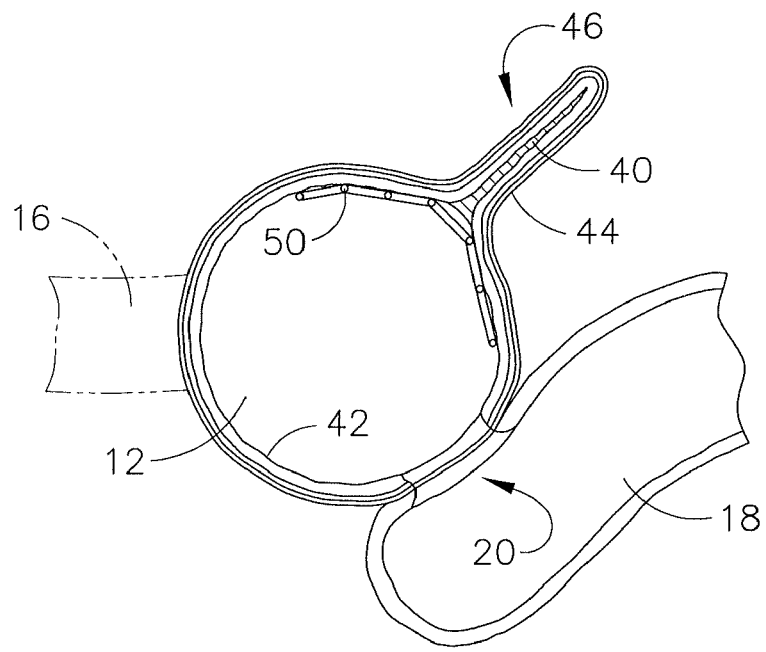
FIG. 7 depicts a cross-sectional view of the stomach of FIG. 4 with an exemplary apposed-wall portion.

In the present example, and as shown in FIG. 6, an adhesive (40) is applied to the inner wall (42) of the first portion (12) of the stomach (10). The adhesive (40) is applied through an endoscope (30) using an adhesive applier (32). The endoscope (30) of the present example is operable to provide light and visualization to the site at which the adhesive (40) is being applied. Any suitable endoscope (30) or applier (32) may be used. Next, as shown in FIG. 7, the outer wall (44) of the first portion (12) of the stomach (10) is drawn out and pinched, thereby creating an apposed-wall portion (46). Apposed-wall portion (46) may be created using a clamp external to outer wall (44) or using any other suitable device or technique. The apposed-wall portion (46) is created such that the adhesive (40) is entrained therein to provide structural integrity for the apposed-wall portion (46). Furthermore, as is also shown in FIG. 7, a mesh (50) may be secured to the inner wall (42) of the first portion (12) adjacent to apposed-wall portion (46) (e.g., over the contraction line at apposed-wall portion (46)) using an adhesive (40). Such a mesh (50) may provide stress relief for apposed-wall portion (46), thereby enhancing the structural integrity of the apposed-wall portion (46).

In the example depicted in FIGS. 6 and 7, the apposed-wall portion (46) provides volume reduction of first portion (12) of the stomach (10), the potential benefits of which will be apparent to those of ordinary skill in the art. While the example is provided in the context of a gastric bypass, it will be appreciated that one or more apposed-wall portions (46) may be provided in a stomach (10) that has not been subject to a gastric bypass procedure. It will also be appreciated that the exemplary method for forming apposed-wall portion (46) may be varied or supplemented in a variety of ways. By way of example only, any suitable substitute structure or substance may be used for mesh (50) and/or for adhesive (40). Still other ways of varying the foregoing embodiments will be apparent to those of ordinary skill in the art.

Figure 8:
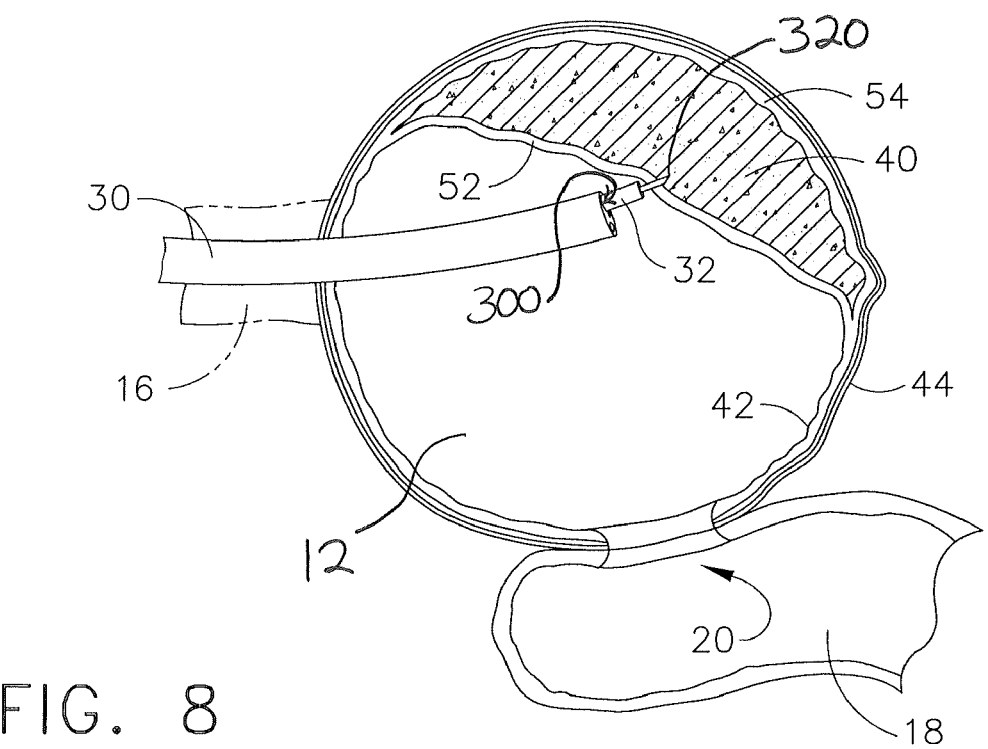
FIG. 8 depicts a cross-sectional view of the stomach of FIG. 4 with an adhesive being injected between the mucosa and muscular layers in an exemplary fashion.
Figure 14:
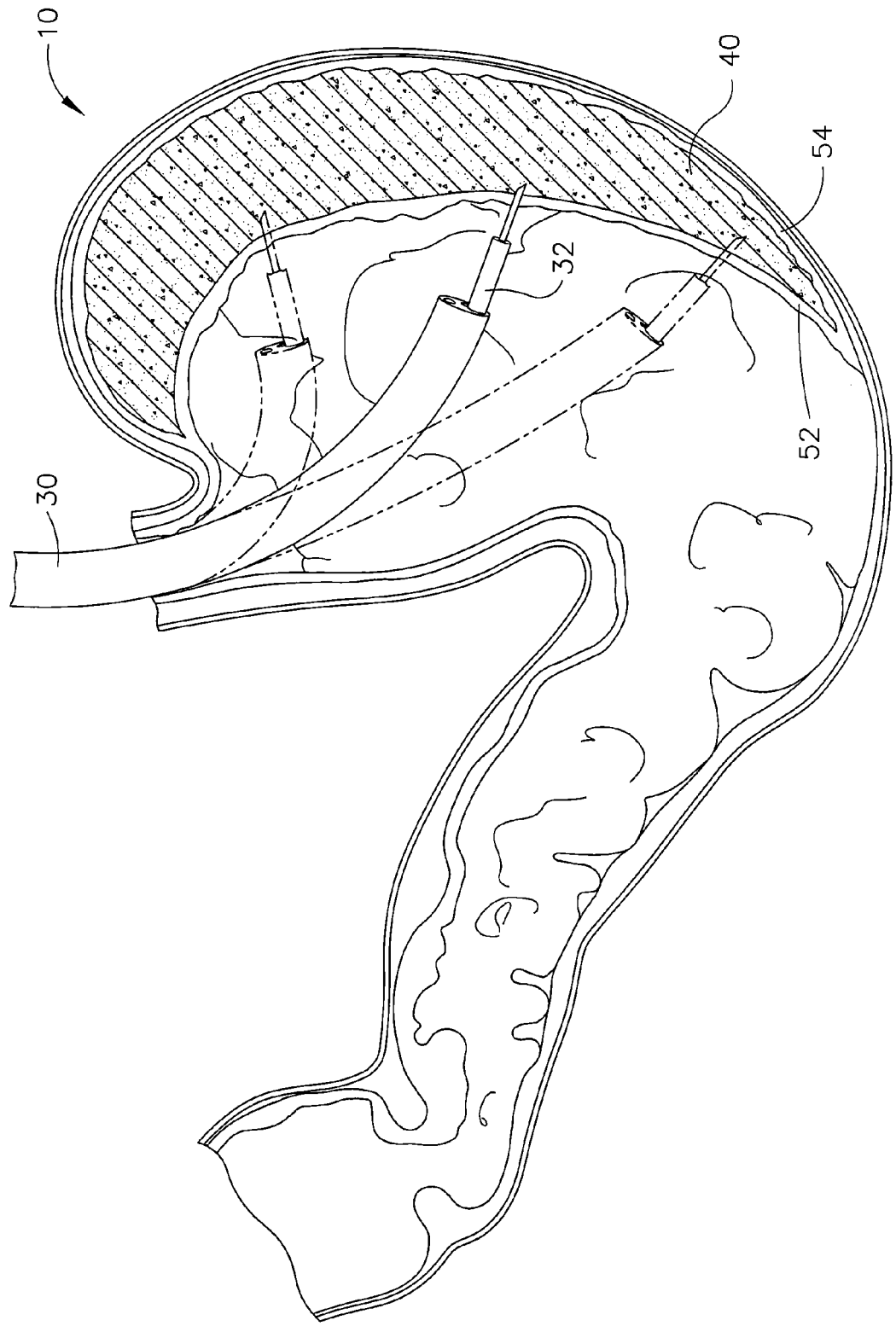
FIG. 14 depicts a cross-sectional view of a patient's stomach with an adhesive being injected between the mucosa and muscular layers in an exemplary fashion.

An alternative to the procedure illustrated in FIGS. 6 and 7 is depicted in FIG. 8. In this embodiment, an endoscope (30) is again used as an imaging device as described above in the context of the example depicted in FIGS. 6 and 7. As shown in FIG. 8, endoscope (30) is introduced into first portion (12) of the stomach (10) via the esophagus (16). As also shown in FIG. 8, applier (32) is received through a working channel (300) formed in endoscope (30), such that a distal portion of applier (32) is introduced into first portion (12) of the stomach (10) via working channel (300). In this example, an adhesive (40) is applied interstitially within first portion (12) of the stomach (10). In particular, adhesive (40) is injected in an interstitial location between a first layer, such as the mucosa (52) or submucosa layer, and an adjacent second layer, such as the muscular layer (54), of the first portion (12) via the tip (320) of applier (32), after the tip (320) of applier (32) is used to penetrate the mucosa (52) layer or submucosa layer of the first portion (12) of stomach (10) as shown in FIG. 8. By way of example only, adhesive (40) may be generally flexible; though it will be appreciated that adhesive (40) may have any other suitable properties. The interstitial application of adhesive (40) may provide volume reduction of first portion (12) of the stomach (10), the potential benefits of which will be apparent to those of ordinary skill in the art. In particular, and as can be clearly seen in FIG. 8, the act of dispensing adhesive (40) separates at least part of the mucosa (52) layer or submucosa layer from the muscular layer (54), urging the separated part of the mucosa (52) layer or submucosa layer inwardly toward a central region within first portion (12) of stomach (10) to reduce an internal volume defined by stomach (10). While the example is provided in the context of a gastric bypass, it will be appreciated that interstitial application of an adhesive (40) may be provided in a stomach (10) that has not been subject to a gastric bypass procedure. An example of such a context is illustrated in FIG. 14. It will also be appreciated that the exemplary method for interstitial application of adhesive (40) may be varied or supplemented in a variety of ways. By way of example only, any suitable substitute substance may be used for adhesive (40). As another variation of the embodiments depicted in FIGS. 8 and 14, adhesive (40) may be applied directly to inner wall (42). If desired, adhesive (40) may be so applied in layers until a desired volume reduction of first portion (12) or stomach (10) is obtained. In yet another variation, adhesive (40) is injected into rugal folds of a stomach (10) wall. Still other ways of varying the foregoing embodiments will be apparent to those of ordinary skill in the art.

Figure 9:
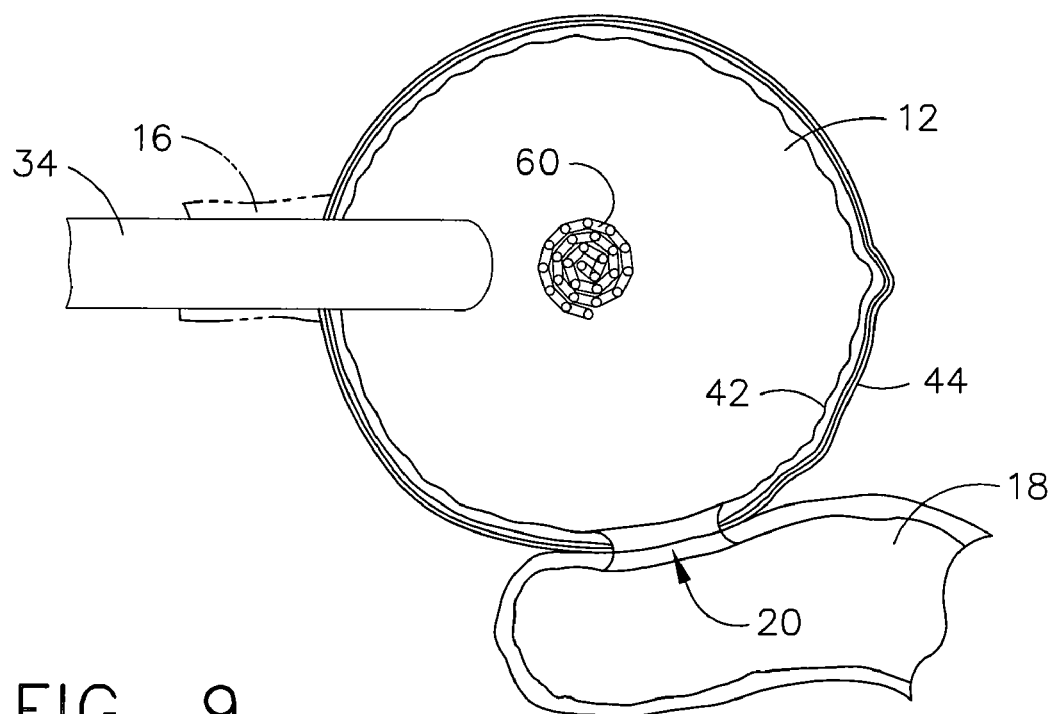
FIG. 9 depicts a cross-sectional view of the stomach of FIG. 4 with an exemplary mesh deployed therein.
Figure 10:
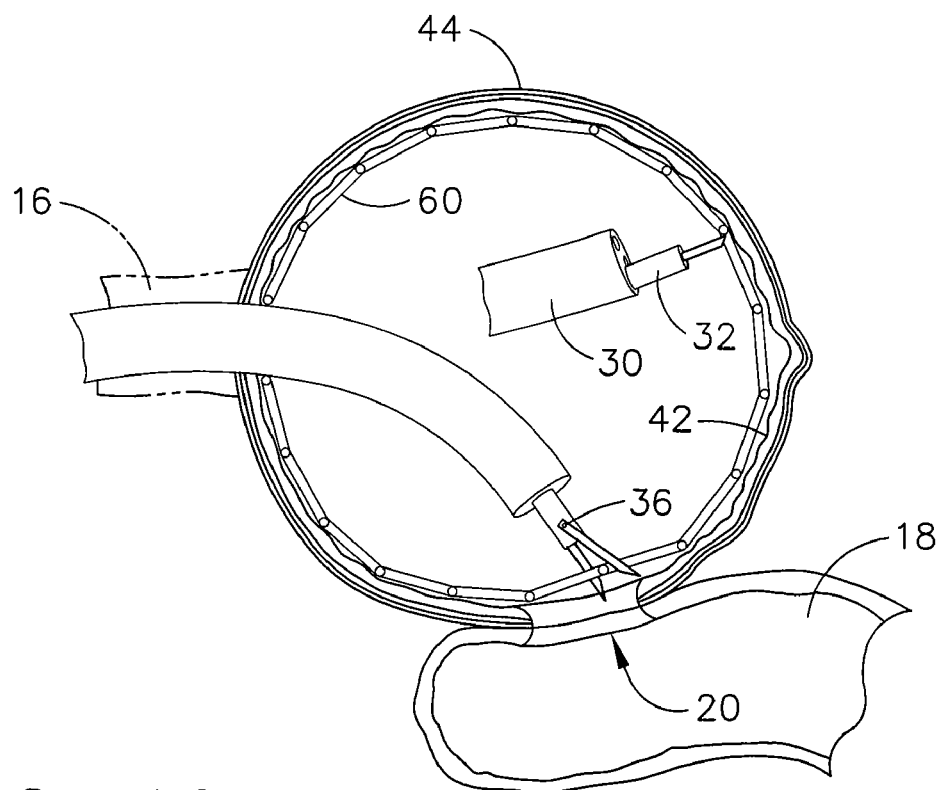
FIG. 10 depicts a cross-sectional view of the stomach of FIG. 4 with the mesh of FIG. 9 being secured to the inner wall of the stomach with an adhesive in an exemplary fashion.

In the embodiment depicted in FIGS. 9 and 10, a delivery tube (34) is introduced to first portion (12) via the esophagus (16). A mesh (60) is deployed through delivery tube (34) into first portion (12). As shown, mesh (60) may be in a generally compacted form (e.g., rolled up, folded up, etc.) upon initial deployment. Other suitable configurations for mesh (60) may be used. In the present example, mesh (60) comprises a flexible yet non-expanding material such as polyester. Alternatively, any other suitable material having any suitable properties may be used for mesh (60). Mesh (60) is then applied to the inner wall (42) of the first portion (12) of the stomach (10). This may include an act of unrolling, unfolding, and/or performing other acts upon mesh (60) and positioning mesh (60) about inner wall (42). Mesh (60) is secured to inner wall (42) using an adhesive (40) applied using an applier (32) through an endoscope (30). It will be appreciated that, over time, mesh (60) may become enveloped in scar tissue, such that adhesive (40) is not necessary to secure mesh (60) to first portion (12). Accordingly, as in various other embodiments described herein, adhesive (40) may be biodegradable or have any other suitable properties.

As is shown in FIG. 10, a cutting device (36) may be used to cut mesh (60) away from the area of anastomosis (20) to prevent mesh (60) from obstructing passage of materials to small intestine (18). The application of mesh (60) to inner wall (42) of first portion (12) may prevent distention of portion (12) of the stomach (10), the potential benefits of which will be apparent to those of ordinary skill in the art. While the example is provided in the context of a gastric bypass, it will be appreciated that the application of a mesh (60) to the inner wall (42) of a stomach (10) may be provided in a stomach (10) that has not been subject to a gastric bypass procedure. It will also be appreciated that the exemplary method for application of mesh (60) may be varied or supplemented in a variety of ways. By way of example only, any suitable substitute structure may be used for mesh (60). Still other ways of varying the foregoing embodiments will be apparent to those of ordinary skill in the art.

Figure 11:
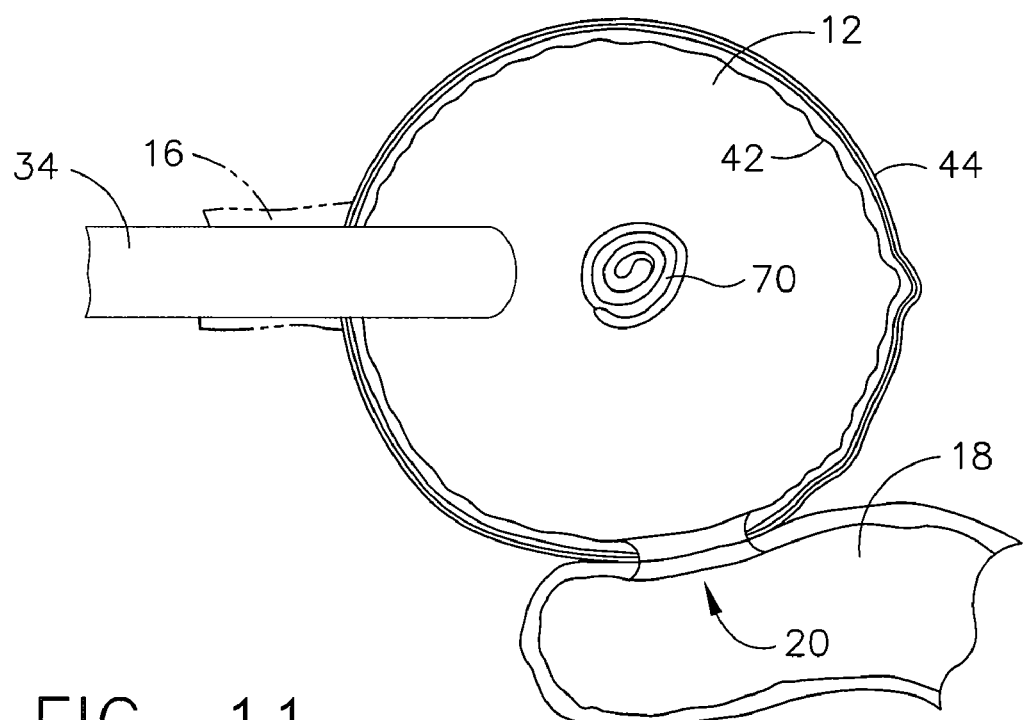
FIG. 11 depicts a cross-sectional view of the stomach of FIG. 4 with an exemplary appliance deployed therein.
Figure 12:
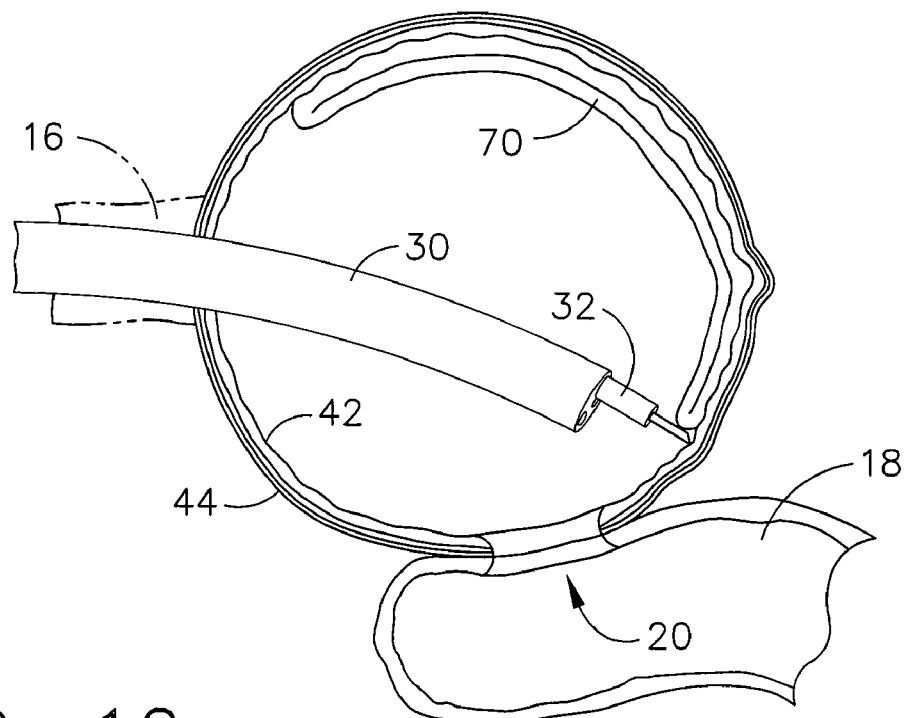
FIG. 12 depicts a cross-sectional view of the stomach of FIG. 4 with the appliance of FIG. 11 being secured to the inner wall of the stomach with an adhesive in an exemplary fashion.
Figure 13:
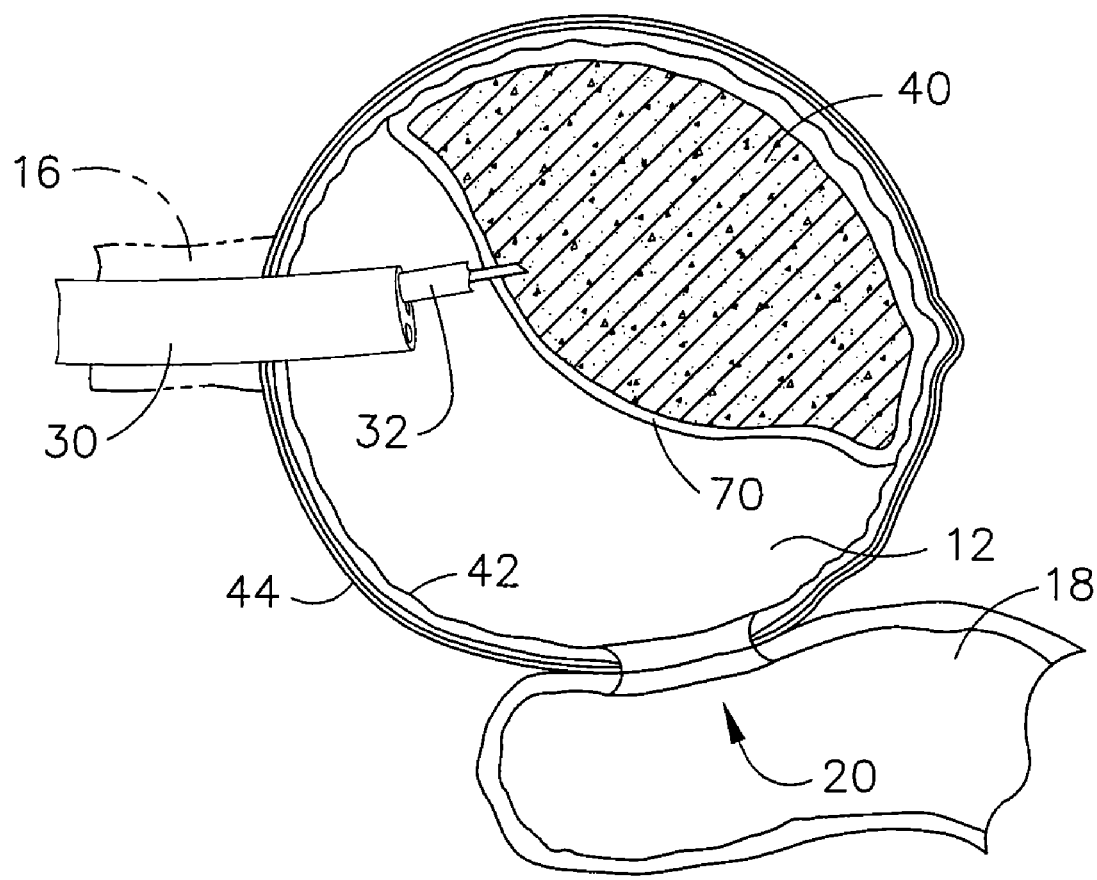
FIG. 13 depicts a cross-sectional view of the stomach of FIG. 4 with the appliance of FIG. 11 being filled with a medium in an exemplary fashion.

In the embodiment depicted in FIGS. 11-13, a delivery tube (34) is introduced to first portion (12) via the esophagus (16). An appliance (70) is deployed through delivery tube (34) into first portion (12). As shown, appliance (70) may be in a generally compacted form (e.g., rolled up, folded up, etc.) upon initial deployment. Appliance (70) of the present example comprises a preformed non-distensible pouch. Other suitable configurations for appliance (70) may be used. In the present example, appliance (70) comprises a flexible non-expanding material such as silicone. Alternatively, any other suitable material having any suitable properties may be used for appliance (70). Appliance (70) is then applied to the inner wall (42) of the first portion (12) of the stomach (10). This may include an act of unrolling, unfolding, and/or performing other acts upon appliance (70) and positioning appliance (70) about inner wall (42). Appliance (70) is secured to inner wall (42) using an adhesive (40) applied using an applier (32) through an endoscope (30).

As shown in FIG. 13, after appliance (70) has been secured to inner wall (42), an adhesive (40) is injected into appliance (70) using an applier (32) through an endoscope (30). By way of example only, adhesive (40) may be generally flexible; though it will be appreciated that adhesive (40) may have any other suitable properties. The injection of adhesive (40) into appliance (70), and the resulting expansion of appliance (70), may provide volume reduction of first portion (12) of the stomach (10), the potential benefits of which will be apparent to those of ordinary skill in the art. While the example is provided in the context of a gastric bypass, it will be appreciated that adhesive (40) may be injected into an appliance (70) provided in a stomach (10) that has not been subject to a gastric bypass procedure. It will also be appreciated that the exemplary method for applying an appliance (70) to inner wall (42), and/or the injection of an adhesive (40) into an appliance (70), may be varied or supplemented in a variety of ways. By way of example only, any suitable substitute substance may be used for adhesive (40). Still other ways of varying the foregoing embodiments will be apparent to those of ordinary skill in the art.

Figure 15:
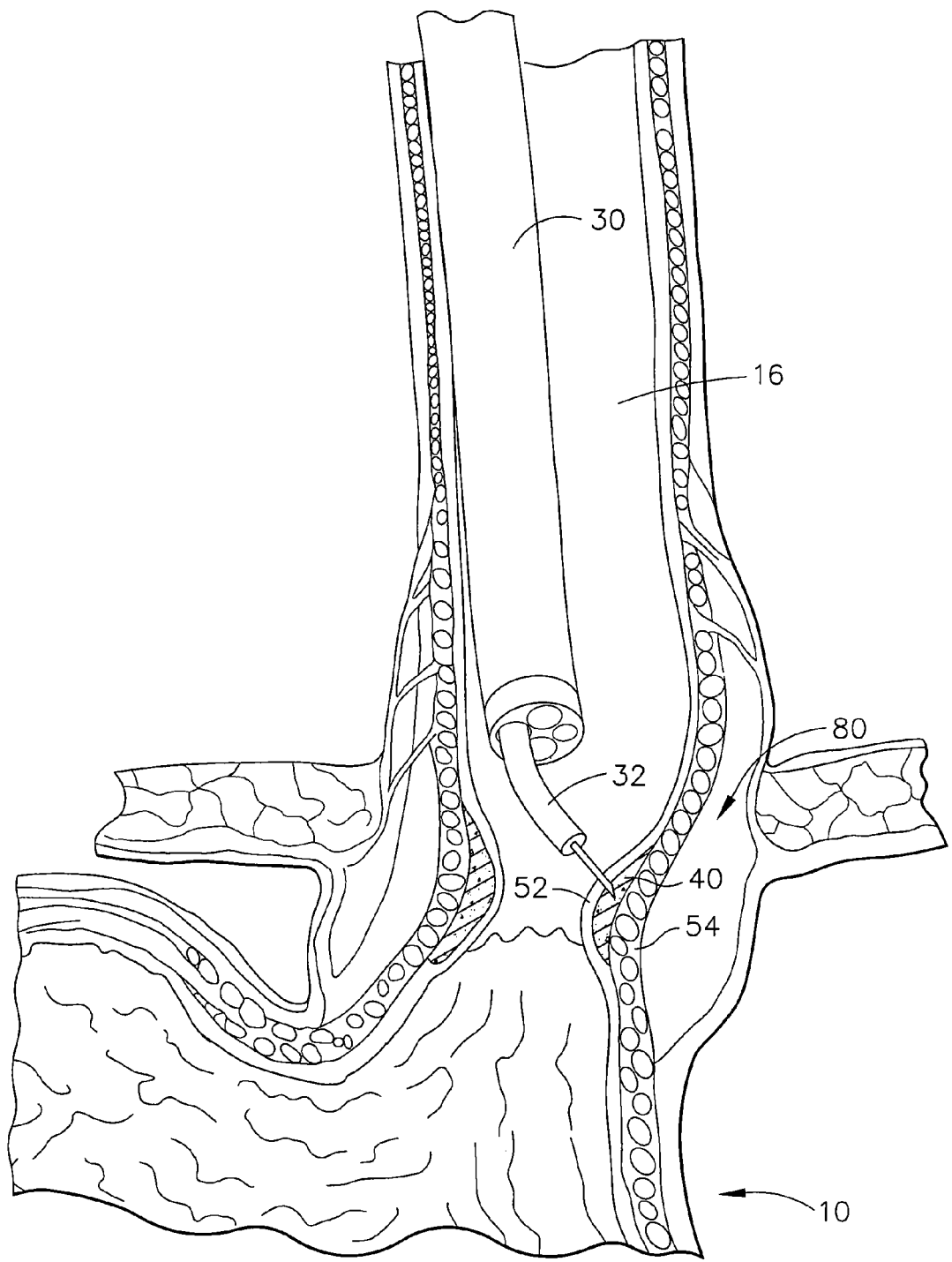
FIG. 15 depicts a cross-sectional view of a patient's gastroesophageal junction with an adhesive being injected between the mucosa and muscular layers in an exemplary fashion.

In the embodiment depicted in FIG. 15, an adhesive (40) is interstitially injected between the mucosa (52) or submucosa and muscular (54) layers of a gastroesophageal junction or cardia (80). The adhesive (40) is injected using an applier (32) through an endoscope (30). The injection may provide a reconstruction of the cardia (80). Such injection may reduce or prevent acid reflux in the patient, may provide an appetite-reducing restriction, and/or may provide other results. Alternatively, any medium other than an adhesive (40) may be used, adhesive (40) may be applied in any other suitable fashion or location, and/or the foregoing technique may be varied in any other suitable way.

Figure 16:
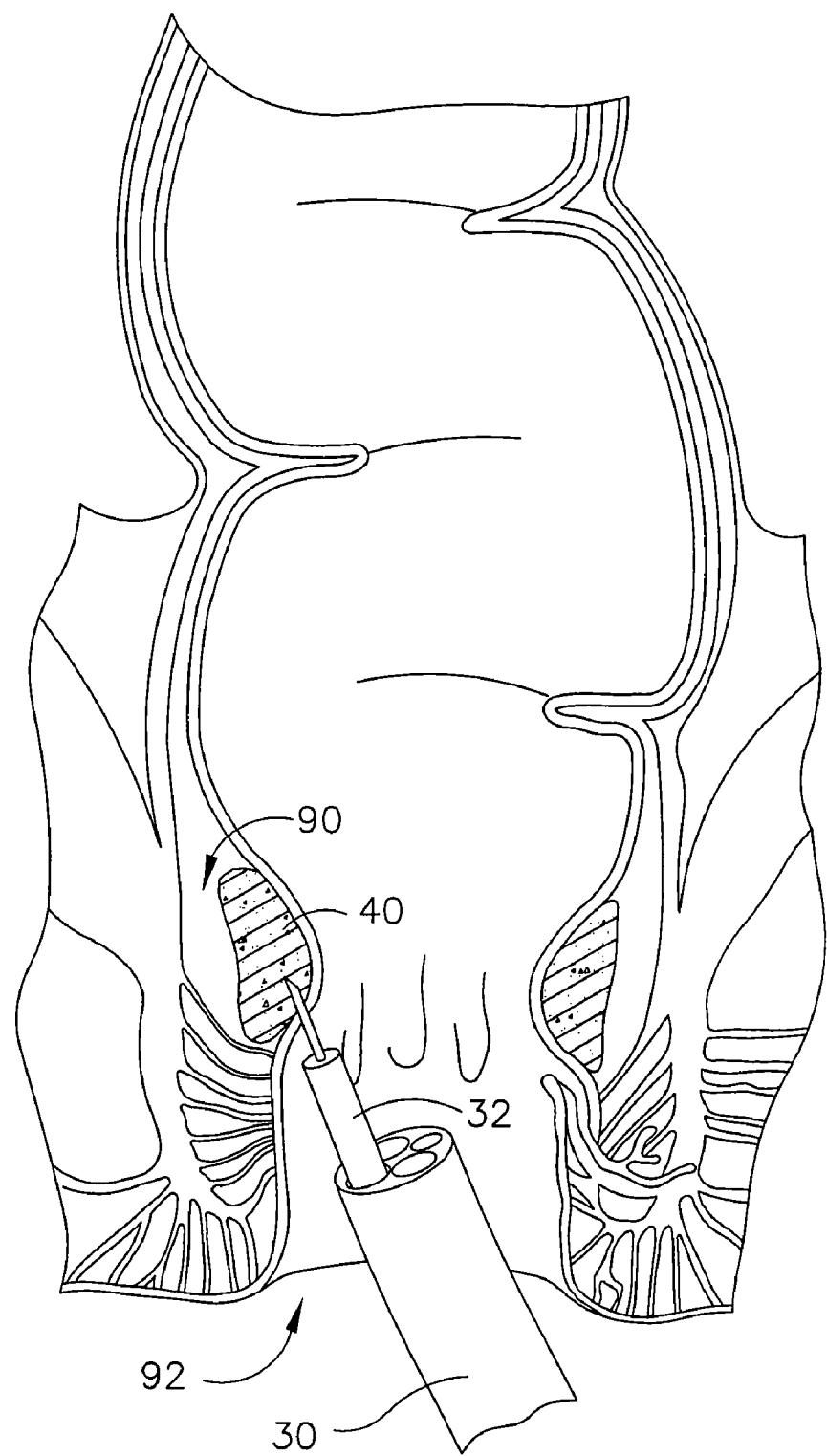
FIG. 16 depicts a cross-sectional view of a patient's rectum with an adhesive being injected in submucous space.

In the embodiment depicted in FIG. 16, an adhesive is interstitially injected in submucous space (90) of a rectum (92). The adhesive (40) is injected using an applier (32) through an endoscope (30). The injection may provide an augmentation of the sphincter area. Such injection may reduce or prevent fecal incontinence, and/or may provide other results. Alternatively, any medium other than an adhesive (40) may be used, adhesive (40) may be applied in any other suitable fashion or location, and/or the foregoing technique may be varied in any other suitable way.

In any of the foregoing embodiments, including variations of the same, adhesive (40) may comprise a cyanoacrylate, an isocyanate, and/or any other suitable substance, including combinations of substances. Furthermore, adhesive (40) may have any suitable properties, including but not limited to flexibility, non-flexibility, hardening capabilities, or any other properties. Adhesive (40) may also comprise an epoxy and/or include the use of an activator substance. Furthermore, it will be appreciated that non-adhesive substances may be used in addition to or in lieu of adhesive (40). Such alternative substances may include, but are not limited to, gels, bulking agents, fluids, or any other suitable substance(s), including combinations thereof. To the extent that an applier (32) or other device has created an access path through tissue in order to dispense adhesive (40) or otherwise, it will also be appreciated that adhesive (40) may be used to seal such a path.

Embodiments of the present invention have application in conventional endoscopic and open surgical instrumentation as well as application in robotic-assisted surgery. While some embodiments have been described as for use in addressing stomach distention, and others have been described as for use in reducing stomach volume, it will be appreciated that embodiments may serve both such purposes, only one of such purposes, or a variety of other purposes. Accordingly, the inventors do not intend that the embodiments described herein be regarded as being limited to the particular uses described herein, or as being limited to serving the particular purposes that have been noted herein. The uses and purposes described herein have been noted for illustrative purposes only.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of reducing the volume of a stomach, wherein the stomach has a first layer comprising a mucosa layer or a submucosa layer and a second layer adjacent to the first layer, the second layer comprising a muscular layer, the method comprising:
   (a) performing a Roux-en-Y gastric bypass procedure, wherein the act of performing a Roux-en-Y gastric bypass procedure comprises:
      (i) separating a first portion of a patient's stomach from a second portion of the patient's stomach, wherein the first portion is adjacent to the esophagus and the second portion is adjacent to the patient's small intestine,
      (ii) forming a pouch with the first portion, and
      (iii) joining the patient's small intestine to the pouch via an anastamosis;
   (b) providing an adhesive applier, wherein the adhesive applier is operable to apply an adhesive;
   (c) providing a biocompatible adhesive;
   (d) introducing at least a portion of the adhesive applier into the first portion of the stomach;

(e) penetrating the first layer of the first portion of the stomach wherein the act of penetrating the first layer of the first portion of the stomach comprises using the adhesive applier to penetrate the first layer of the first portion of the stomach; and (f) dispensing the adhesive through the adhesive applier into the first portion of the stomach to reduce or restrict the volume of the first portion of the stomach, wherein the act of dispensing the adhesive comprises dispensing the adhesive in an interstitial location between the penetrated first layer of the first portion of the stomach and the second layer of the first portion of the stomach adjacent to the first layer, wherein act of dispensing is performed after the act of performing the Roux-en-Y gastric bypass procedure.

2. The method of claim 1, wherein the adhesive is generally flexible.

3. The method of claim 1, the method further comprising introducing an imaging device into the stomach.

4. The method of claim 3, wherein the imaging device is introduced into the stomach via an esophagus.

5. The method of claim 3, wherein the imaging device comprises an endoscope.

6. The method of claim 3, wherein the imaging device has a working channel configured to receive a medical instrument, wherein the at least a portion of the adhesive applier is introduced into the stomach via the working channel.

7. The method of claim 1, wherein the adhesive applier is operable to inject the adhesive after penetrating the first layer of the first portion of the stomach, wherein the act of dispensing the adhesive comprises using the applier to inject the adhesive after the act of using the applier to penetrate the first layer of the first portion of the stomach.

8. The method of claim 1, wherein the stomach has a plurality of rugal folds, wherein the act of dispensing the adhesive comprises injecting the adhesive into one or more of the rugal folds.

9. The method of claim 1, wherein the act of dispensing the adhesive comprises dispensing the adhesive at a plurality of locations within the stomach.

10. The method of claim 1, wherein the act of dispensing the adhesive separates at least part of the first layer from the second layer, urging the separated part of the first layer inwardly toward a central region within the stomach to thereby reduce an internal volume defined by the stomach.

11. A method of reducing the volume of a stomach, wherein the stomach has a submucosa layer and a muscle layer, the method comprising;

(a) performing a Roux-en-Y gastric bypass procedure, wherein the act of performing a Roux-en-Y gastric bypass procedure comprises:
  (i) separating a first portion of a patient's stomach from a second portion of the patient's stomach, wherein the first portion is adjacent to the esophagus and the second portion is adjacent to the patient's small intestine,
  (ii) forming a pouch with the first portion, and
  (iii) joining the patient's small intestine to the pouch via an anastomosis;

(b) providing an adhesive applier, wherein the adhesive applier is operable to apply an adhesive;

(c) providing a biocompatible adhesive;

(d) introducing at least a portion of the adhesive applier into the first portion of the stomach, wherein the at least a portion of the adhesive applier is introduced into the first portion of the stomach via an endoscope;

(e) penetrating the submucosa layer of the first portion of the stomach to reach an interstitial location between the submucosa layer and the muscle layer; and (f) dispensing the adhesive through the adhesive applier into the interstitial location between the penetrated submucosa layer and the muscle layer of the first portion, wherein act of dispensing is performed after the act of performing the Roux-en-Y gastric bypass procedure.

* * * * *